United States Patent [19]

Fields

[11] 4,155,958
[45] May 22, 1979

[54] BETA-PHOSPHOSULFOXY ALCOHOLS

[75] Inventor: Ellis K. Fields, River Forest, Ill.

[73] Assignee: Standard Oil Company (Indiana), Chicago, Ill.

[21] Appl. No.: 836,398

[22] Filed: Sep. 26, 1977

[51] Int. Cl.$^2$ .............................................. C07F 9/17
[52] U.S. Cl. .................................... 260/926; 260/934; 204/158 R
[58] Field of Search .............................. 260/934, 926; 204/158 R

[56] References Cited

U.S. PATENT DOCUMENTS

| 2,910,500 | 10/1959 | Schrader et al. | 260/934 |
| 3,179,688 | 4/1965 | Maier | 260/926 |
| 3,454,679 | 7/1969 | Aichenegg et al. | 260/934 |

*Primary Examiner*—Anton H. Sutto
*Attorney, Agent, or Firm*—William C. Clarke; Arthur G. Gilkes; William T. McClain

[57] ABSTRACT

Beta-phosphosulfoxy alcohols and preparation thereof by reacting an olefinically unsaturated compound and a poly-thiophosphoric acid with oxygen using actinic radiation as an energy source at a temperature of from −10° to 70° C., preferably in the presence of a dye sensitizer.

11 Claims, No Drawings

BETA-PHOSPHOSULFOXY ALCOHOLS

BACKGROUND OF THE INVENTION

The field of this invention relates to a novel class of beta-phosphosulfoxy alcohols and a method for preparing these beta-phosphosulfoxy alcohols by reacting a poly-thiophosphoric acid, an olefinically unsaturated compound and oxygen using actinic radiation as an energy source preferably in the presence of a dye sensitizer. These compounds are surface active agents which have biocidal activity and are suitable for surfactants, soluble oils and anti-wear additives.

Organic sulfur compounds are of considerable industrial importance. Novel organic sulfur compounds with characteristics suitable for use in surfactants, soluble oil compositions, tertiary oil recovery, micellar fluids, antiwear additives, and miscellaneous uses such as pesticides are of extensive utility. For example, steam turbine and other industrial oils can be stabilized by use of surfactants against the rusting of ferrous parts should water become mixed with the oil. An important use of soluble oils is as lubricating and cooling agents in the cold working of metals such as in grinding, cutting, and threading operations. For this use, the soluble oil is dispersed in from about 10 to 80 or more times its own volume of water and circulated over the contact point of the working tool and the metal being worked upon. Frequently, difficulty is encountered in this type of operation due to the tendency of the soluble oil emulsion or dispersion to cause rusting of metals in contact with such emulsions, particularly ferrous metals and also because in the course of time, these emulsions or dispersions develop strong, putrid undesirable odors if the soluble oil composition does not contain a bactericide. Many anti-wear additives for use in motor oils and other lubricants are based on metals, as for example, zinc dithiophosphate.

The use of non-metal-containing anti-wear additives for motor oils is highly desired to reduce atmospheric metals pollution through the engine exhaust or blow-by.

DESCRIPTION OF THE PRIOR ART

This invention relates to beta-phosphosulfoxy alcohols, to a method for their preparation and to their use as surface active agents which have biocidal activity and anti-wear additive properties.

Beta-hydroxyalkylsulfoxides have been obtained; a mercaptan can be reacted with an olefin in the presence of oxygen. Anderson, U.S. Pat. No. 3,247,258, which is incorporated by reference, discloses that beta-hydroxyalkylsulfoxides can be obtained in good yields by reacting the mercaptan, olefin, and oxygen at a temperature above 80° C. as substantially no reaction occurs below that temperature. With certain olefins and mercaptans such as indene, styrene and thiophenol, the reaction occurs first by mixing the olefin and the mercaptan with the oxygen being bubbled thereafter through the mixture. Other patents such as Oswald et al, U.S. Pat. No. 3,043,824 and Goodhue et al, U.S. Pat. No. 3,210,243, which are each incorporated by reference, disclose preparing beta-hydroxyalkylsulfoxides through (1) a co-oxidation route using a hydroperoxide or through (2) oxidation of the sulfide by means of hydrogen peroxide. Oswald indicates that preparation of hydroperoxide products by olefin-mercaptan co-oxidation to the sulfoxide requires a chain initiator, e.g., ultraviolet light or the addition of peroxide compounds (hydroperoxides). Goodhue teaches the preparation of the sulfoxide using hydrogen peroxide in a three-step synthesis through the sulfide which in turn is prepared from the mercaptan with epichlorohydrin.

However, in the prior art as it pertains to beta-hydroxyalkylsulfoxides, there has been no teaching that beta-phosphosulfoxy alcohols can be prepared from poly-organo thiophosphoric acids and olefinically unsaturated compounds in the presence of oxygen, using actinic radiation as an energy source preferably in the presence of a dye sensitizer.

Although the preparation of 0,0,S-trialkylthionophosphates by the addition of 0,0-dialkyl thiolthionophosphates to olefins is well-known in the prior art, (J.A.C.S., 74, 161 (1952); Norman et al, U.S. Pat. No. 2,802,856, which are incorporated by reference), the preparation of beta-phosphosulfoxy alcohols by the addition of poly-organo-thiophosphoric acids to olefinically unsaturated compounds is not known.

It is known that di-organo-thiophosphoric acids react with unsaturated organo compounds, if the unsaturated linkage occurs in an essentially straight carbon atom chain which has at least 4 carbon atoms or if the unsaturated linkage is activated by an activating substituent, or if the carbon atom chain has less than 4 carbon atoms under certain special conditions of temperature and pressure. The reaction products of the di-organo-thiophosphoric acids and the unsaturated hydrocarbon compounds are 0,0,S-trialkylthionophosphates or tri-esters of a thiophosphoric acid. This invention is concerned with the discovery that if poly-organo-thiophosphonic acids are reacted at certain temperatures with unsaturated organo compounds in the presence of oxygen and with actinic radiation (visible or ultraviolet light) as an energy source, preferably in the presence of a dye sensitizer, a beta-phosphosulfoxy alcohol of the general structure

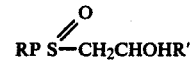

results instead of a tri-ester of the thiophosphonic acid of the general structure RPS CH$_2$CH$_2$R' as is taught in the prior art.

It is therefore, an object of this invention to provide a process for the preparation of beta-phosphosulfoxy alcohols and a novel class of beta-phosphosulfoxy alcohols. Other objects and advantages will become apparent as the following description proceeds.

SUMMARY OF THE INVENTION DETAILED DESCRIPTION

This invention relates to beta-phosphosulfoxy alcohols and a method for their preparation by reacting an olefinic unsaturated compound and a poly-organo-thiophosphoric acid with oxygen using actinic radiation as an energy source at a temperature of −10° to 70° C., preferably in the presence of a dye sensitizer.

DETAILED DESCRIPTION OF THE INVENTION

In general, this invention relates to novel beta-phosphosulfoxy alcohols of thiophosphoric acids of the following general formula

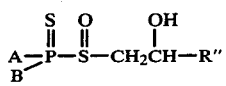

and to a method of producing these alcohols which comprises reacting:

(a) thiophosphoric acids of the following structure:

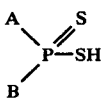

wherein A is selected from the class consisting of RO— and RS—, B is selected from the group consisting of R'O— and R'S—, and R and R' are individually selected from the group consisting of hydrogen and aliphatic groups of from 1 to 24 carbon atoms; with (b) olefinic unsaturated aliphatic hydrocarbon compounds of at least 2 carbon atoms to 24 carbon atoms having at least one unsaturated double bond; and wherein R'' is hydrogen or an aliphatic straight carbon atom chain of 1 to 22 carbon atoms; within a temperature range of from −10° C. to 70° C., in such proportions as to cause the reaction to proceed at a reasonable rate; preferably in the presence of a dye sensitizer, with sufficient oxygen to react with the olefin and the thiophosphoric acid with actinic radiation (visible or ultraviolet light) as an energy source.

This invention also relates to a process for preparing beta-phosphosulfoxy alcohols by reacting an olefinically-unsaturated compound containing 2 to 30 carbon atoms and a poly-thiophosphoric acid containing 2 to 48 carbon atoms, wherein the olefinically-unsaturated compound and the poly-thiophosphoric acid are defined as above, with oxygen using actinic radiation as an energy source at a temperature within the range from about −10° to 70° C.

Although the stiochiometry of the process involves one mole of (a) with one mole of (b), it is apparent to one skilled in the art that these proportions can be altered. For example, it can be desirable to employ an excess of the unsaturated reactant (b) so as to force the reaction to substantial completion. Using styrene as reactant (b) for purposes of illustration, the reaction proceeds according to the equation:

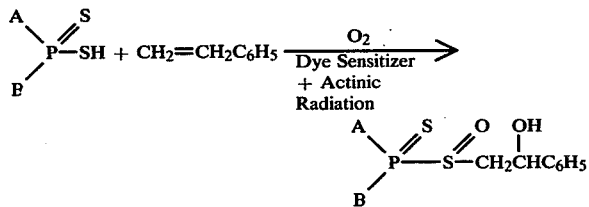

More particularly, this invention relates to novel beta-phosphosulfoxy alcohols and to a method of producing beta-phosphosulfoxy alcohols from thiophosphoric acids which comprises reacting: (a) O,O-poly-organo dithiophosphoric acids of the following structure

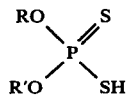

wherein R and R' are selected from the group consisting of the same or different aliphatic groups of from 1 to 24 carbon atoms with (b) olefinically unsaturated compounds of at least one unsaturated linkage in an essentially straight carbon atom chain of 2 carbon atoms to 24 carbon atoms which can be unsubstituted or substituted so long as the substitutions do not interfere with the course of the reaction. Typical groups which can be attached to the straight carbon atom chain of the olefinically unsaturated compound are alkyl groups of 1 to 3 carbon atoms, phenyl, naphthyl, anthranyl, and phenanthryl groups, halogens such as fluorine, chlorine, iodine, and bromine, nitro groups, aralkoxy groups such as phenoxy, p-cresyloxy, 2-napthoxy, and heterocyclic groups such as furyl, thienyl, benzothienyl, and pyridyl. Examples of the olefins used in my invention are ethylene, propylene, cis-2-butene; 1-octene; 1-dodecene; disisobutylene; styrene; m- and p-chlorostyrene; 2-vinylnaphthalene; 1,3-butadiene; 1,4-pentadiene; 4-vinylcyclohexene-1, as well as olefin polymers such as polybutene and the polypropylenes. Examples of the di-thiophosphoric acids are dimethyl dithiophosphoric acid or dimethyl DPA, diethyl DPA, dibutyl DPA, diamyl DPA, di-isoamyl DPA, di-iso-octyl DPA, diphenyl DPA, bis-p-chlorophenyl DPA, di-4-nitrophenyl DPA, dioctyl tetrathiophosphoric acid or dioctyl TPA, diphenyl TPA, di-4-bromophenyl TPA, and di-4-quinolyl TPA.

Accordingly, it is the general object of this invention to produce beta-phosphosulfoxy alcohols directly from poly-organo-thiophosphoric acids in good yield at ambient temperatures by co-oxidation with an olefinically unsaturated compound using oxygen and actinic radiation (visible or ultraviolet light) as an energy source preferably in the presence of dye sensitizer. If visible light is used, the dye sensitizer can be selected from the group consisting of methylene blue, Eosin and Rose Bengal, preferably in acetone solution.

For the purpose of this invention, it is essential that actinic radiation preferably in conjunction with a dye sensitizer be used to obtain good product yields. If actinic radiation either in the form of ultraviolet or visible light is not employed, yields of beta-phosphosulfoxy alcohols are substantially lower, as is evidenced in Example XII, wherein a control solution contained a dye sensitizer but which was unexposed to actinic radiation from illumination resulted in either little or no co-oxidation products.

In general, the process for preparing beta-phosphosulfoxy alcohols requires the reacting of an olefinically unsaturated compound containing 2 to 30 carbon atoms with a poly-thiophosphoric acid of from 2 to 48 carbon atoms in the presence of oxygen. The olefinically unsaturated compounds can be aliphatic, aromatic, cyclic, and heterocyclic compounds. These compounds are preferably terminal olefins with the double bond in the 1-position and can be visualized as being of the formula R''CH=CHR''' where R''' is preferably hydrogen. However, R'' and R''' can be defined also as radicals and can be the same or different straight chain or branched chain alkyl groups containing 1 to 22 carbon atoms (such as methyl, ethyl, i-butyl, octyl, etc., to docosyl groups), preferably 4 to 10 carbon atoms; aralkyl groups as beta-phenethyl, alkylated aryl groups as tolyl or xylyl, heterocyclic alkyl groups as picolyl and thiazylmethyl, cycloalkyl groups as cyclopentylmethyl and cyclohexylmethyl, the last four containing 5 to 30 carbon atoms, preferably 6 to 24 carbon atoms, and the same groups containing substituents such as halogens (fluorine, chlorine, bromine, and iodine), nitro, alkoxy (methoxy, ethoxy, propoxy, butoxy) or dialkylamino groups. R" and R'" can be joined and comprise a ring containing five to eight carbon atoms. Examples where R" and R'" are so joined to comprise a ring are cyclopentadiene and cyclooctatetraene. Examples of olefinically unsaturated aliphatic, aromatic and alicyclic compounds are ethylene, propylene, 1-butene, 1-pentene, 1-hexene, 1-octene, 1-decene, 1-dodecene, cyclohexene, cyclopentene, cyclooctene, cyclododecene, bicycloheptene, octahydronaphthalene, styrene, alpha-methylstyrene, 3-phenyl-1-propene, 1,1-diphenylethylene, 3,4-diphenylbutene-1, 1- and 2-vinylnaphthalene, 4-vinylbiphenyl, 1-vinyl anthracene, 2- and 4-vinylpyridine, 3-vinylthiophene, 2-vinylfuran, 2- and 4-vinylquinoline, 1-vinylphenanthridene, 2-vinyl-1,3,5-triazene.

Preferably the olefinically unsaturated compound comprises a hydrocarbon containing 2 to 16 carbon atoms in a carbon-to-carbon chain such as ethylene, butene-1, tetradecene-1, hexadecene-1, or styrene. These are preferred because they are cheap and react readily, comprising easily available compounds for providing a range of derivative short-chain water-soluble compounds to long-chain oil-soluble compounds.

The polythiophosphoric acid compound can contain from 2 to 48 carbon atoms and can be an aliphatic, aromatic, alicyclic and heterocyclic compound and can be described as being of the general formula

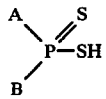

wherein A and B are individually selected from the group consisting of RO— and R'S— and R and R' are selected from the group consisting of the same or different organic radicals. R and R' can be an alkyl group of from 1 to 24 carbon atoms, of methyl to tetracosyl groups, preferably 1 to 16 carbon atoms. Examples of such polythiophosphoric acid compounds are as already given above.

Preferably the polythiophosphoric acid compound comprises an acid containing 2 to 16 carbon atoms. These are preferred because they are cheap, reactive and extend the range of derivatives to cover those soluble in various inorganic and organic solvents. One or more hydrogens of the aliphatic, alicyclic and aromatic moieties such as methyl, ethyl, isobutyl, tolyl and phenyl moieties of the above described thiol compounds can be replaced with non-reactive radical groups such as halogens and nitro radicals and, on the alicyclic and aromatic moieties, by alkyl moieties.

The molar ratios of the reactants i.e., the polythiophosphoric acids, olefinically unsaturated compounds, oxygen, that can be used, can vary considerably. The acid: olefin ratio is between 0.001 to 5 moles of acid per mole of olefin. In the practice of my invention substantially equimolar amounts of olefin and acid are preferred. Use of a solvent such as heptane, hexane, benzene, acetone, or dioxane at concentrations of 1 to 85 weight percent is convenient.

Heptane is the preferred solvent: 10 to 40 weight percent is the preferred concentration range of the reactants.

In the practice of my invention it is preferable that at least one optically sensitizing dye be used in conjunction with the application of actinic radiation. For purposes of my invention, the term dye sensitizer can be defined as being an organic dye which increases spectral response. Typical dye sensitizers are fluorescein derivatives, methylene blue, certain porphyrins and polycyclic aromatic hydrocarbons. For purposes of this invention, suitable dye sensitizers include Rose Bengal, methylene blue and Eosin.

Rose Bengal and methylene blue are the preferred dye sensitizers dissolved in acetone at 0.1–5% by weight. Sufficient dye is added to give final concentrations of 0.02 to 1% by weight in the total reaction mixture: 0.05 to 0.25% by weight is preferred. Alternatively the dye may be introduced bound to an ion-exchange resin in a relatively insoluble form, e.g. anionic Rose Bengal or Eosin attached to the strongly basic anion exchange resin Amberlite IRA-400 (Rohm and Haas, Philadelphia) or cationic methylene blue attached to the strongly acidic cation exchange resin Amberlite IRC-200 (J. R. Williams et al., *Tetrahedron Letters* 4603 (1973)).

My reaction can be run in any type of open or sealed vessel, suitably agitated. A particularly useful apparatus for the reaction is the Parr Pressure Reaction Apparatus, Item #3911, made by Parr Instrument Company of Moline, Illinois. This apparatus consists of a heavy-walled clear pyrex bottle connected with a tank of oxygen under pressure; the bottle is shaken vigorously during the reaction. Pressures of oxygen of 1 to 250 psig may be used; 15 to 50 psig $O_2$ are convenient pressures in the laboratory although, commercially, pressures over 100 psig are preferred. The bottle is irradiated with ultraviolet or visible light such as from ultraviolet lights or sunlamps or ordinary incandescent or photoflood bulbs of 50–500 watts, preferably mounted in reflectors with the light source 1½ to 3 inches from the vessel. The actinic radiation is within the range of from about 200 nanometers to about 800 nanometers or from 2000 Angstroms (A°) to 8000 A°.

The lamps used were General Electric 500 watt photoflood or incandescent bulbs and a General Electric 275 watt Sunlamp. Specifications of the G.E. 500 watt photoflood lamp require 1.61 radiated watts from 280 to 400 nanometers, and 6.9 radiated watts from 400 to 700 nanometers, the range of visible light. The G.E. Sunlamp has 4.47 radiated watts in the ultraviolet range from 280 to 400 nanometers, and 7.03 radiated watts in the visible light range of 400 to 700 nanometers.

Reaction is continued until the calculated amount of oxygen has been absorbed as shown by pressure drop; times of 1 to 100 hours may be used, depending on the nature of the olefin, the acid, and the pressure of oxygen. Workup generally consists of evaporating the reaction mixture at 30°–60° C. and 0.1–1 Torr, conveniently in a rotating RINCO evaporator (BUCHI Vacuum Rotary Evaporator ROTAVAPOR 1, Rinco Instrument Company, Inc., Greenville, Illinois).

In order to facilitate a clear understanding of the invention, the process of preparing beta-phosphosulfoxy alcohols from the reaction product of an olefinically unsaturated compound and an acid compound with the use of oxygen, the following specific embodiments are described in detail. It should be understood, however, that the detailed expositions of the application of this process, while indicating preferred embodiments, are given by way of illustration only since various charges and modifications within the spirit and scope of the invention will become apparent to those skilled in the art from this detailed description.

EXAMPLE I

A mixture of 22.2 g (0.1 mole) of phosphorous pentasulfide, 43.2 ml (0.4 mole) of n-amyl alcohol and 50 ml of n-heptane was stirred and refluxed until all the phosphorus pentasulfide had reacted; this took about 2 hours. The solution was allowed to cool to 50° C., blown with a stream of $N_2$ until all hydrogen sulfide had gone, diluted with 50 ml n-heptane, and cooled to 25° C. The acid was O,O-diamyl phosphorus dithioic acid. It was added to 23 ml (0.2 mole) freshly distilled styrene plus 10 ml 1% methylene blue in acetone, and the mixture was shaken in a Parr Shaker instrument under 24 psig $O_2$ and illumination with 275 watt sunlamp bulb in a reflector. In 4 hours the mixture absorbed 15 lb. $O_2$. It was filtered and evaporated in a rotary evaporator at 40° C. and 0.2 Torr. to give 74.2 g (91.4% yield) of viscous light-brown liquid product, 1-(O,O-diamyl thiophosphoryl sulfoxy)-2-phenyl-2-ethanol,

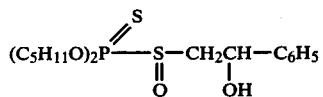

Anal.: Calculated for $C_{18}H_{31}PO_4S_2$, 406 mol. wt., C, 53.2%; H, 7.6%; S, 15.8%; P, 7.6%
Found: C, 53.8%; H, 7.8%; S, 15.2%; P, 7.7%

The infrared spectrum had a strong absorption band at 3300 cm$^{-1}$ characteristic for —C—OH, and a moderate absorption band at 1040 cm$^{-1}$, characteristic of

The mass spectrum showed, as expected, only a tiny peak of mass 406, and much larger peaks at P —$H_2O$, (parent ion minus water) mass 388, and protonated P —$H_2O$, mass 389. Protonated peaks are usual with species containing the hetero atoms O and S. Authentic esters of dithiophosphoric acids characteristically show little or no peaks at the masses of molecular ions, and introduction of oxygen into the ester groups destabilizes the molecular ions still further.

EXAMPLES II TO VI

A mixture of 111 g (0.5 mole) of phosphorous pentasulfide, 200 ml of n-heptane, and 216.9 ml (2 moles) of isoamyl alcohol, 3-methyl-1-butanol, was stirred and refluxed till all the solid had reacted and dissolved, 2.5 hours. The hot solution was blown with a stream of nitrogen to remove hydrogen sulfide, cooled to 25° C., filtered, and diluted to 1 liter with n-heptane in a volumetric flask to give a 1 molar solution of 0,0-di-isoamyl phosphorus dithioic acid,

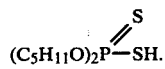

Mixtures of 200 ml (0.2 mole) 1 M diisoamyl phosphorus dithioic acid, 10 ml 1% methylene blue in acetone, and olefins were shaken in a Parr shaker under 24 psig $O_2$ and irradiation with a 275 watt sunlamp bulb in a reflector until $O_2$ absorption ceased. The filtered solutions were evaporated in a Rinco evaporator at 40° C. and 0.5 Torr.

Table I

Table I lists the olefins used and products formed.

Beta-Phosphosulfoxy Alcohols From O,O-Diisoamyl Phosphorus Dithioic Acid and Olefins

| Example | Olefin (Moles) | $O_2$ Uptake, Lbs. | Hrs. | Product, g | Description |
|---|---|---|---|---|---|
| II | Styrene (0.2) | 15 | 8 | 74.8 | Light-yellow viscous oil |
| III | 1-Octene (0.2) | 14 | 8 | 75.8 | Light-brown viscous oil |
| IV | 1,5-Hexadiene (0.1) | 15 | 8 | 58.1 | Brown oil (some loss on workup) |
| V | 4-Vinylcyclohexene-1 (0.2) | 13 | 8 | | |
| | | 19 | 21 | 80.3 | Viscous brown oil |
| VI | 4-Vinylcyclohexene-1 (0.1) | 16 | 8 | | |
| | | 22 | 21 | 82.9 | Very viscous brown oil |

| Example | Names of Products |
|---|---|
| II | 1-(O,O-diisoamyl thiophosphoryl sulfoxy)-2-phenyl-2-ethanol |
| III | 1-(O,O-diisoamyl thiophoshoryl sulfoxy)-2-octanol |
| IV | 1,6-bis (O,O-diisoamyl thiophosphoryl sulfoxy) hexane-2,5-diol |
| V | 1-(O,O-diisoamyl thiophosphoryl sulfoxy)-2-(3-cyclohexenyl-1)-2-ethanol |
| VI | 1-(O,O-diisoamyl thiophosphoryl sulfoxy)-2-[4-hydroxy-3-(O,O-diisoamyl thiophosphoryl sulfoxy)-cyclohexyl]-2-ethanol |

| Elemental Analyses of Products, Examples II - VI | | | | |
|---|---|---|---|---|
| Product | C | H | S | P |
| Example II | | | | |
| Calcd. for $C_{18}H_{31}PO_4S_2$: | 53.2 | 7.6 | 15.8 | 7.6 |
| Found: | 53.8 | 8.0 | 16.2 | 7.5 |
| Example III | | | | |
| Calcd. for $C_{18}H_{39}PO_4S_2$: | 52.2 | 9.4 | 15.5 | 7.5 |
| Found: | 52.8 | 8.9 | 15.9 | 7.1 |
| Example IV | | | | |
| Calcd. for $C_{26}H_{56}P_2O_6S_4$: | 45.5 | 8.2 | 18.7 | 9.0 |
| Found: | 46.2 | 8.7 | 19.5 | 8.6 |
| Example V | | | | |
| Calcd. for $C_{18}H_{35}PO_4S_2$: | 52.7 | 8.5 | 15.6 | 7.6 |
| Found: | 53.3 | 8.0 | 15.8 | 6.9 |
| Example VI | | | | |
| Calcd. for $C_{28}H_{58}P_2O_8S_4$: | 47.2 | 8.1 | 18.0 | 8.7 |
| Found: | 47.9 | 7.9 | 17.2 | 8.0 |

The products of Examples II-VI all showed bands in the infrared spectra at 3300 cm$^{-1}$ for C—OH and 1040 cm$^{-1}$ for —S=O absorptions.

The products of Examples II-VI all showed bands in the infrared spectra at 3300 cm$^{-1}$ for C—OH and 1040 cm$^{-1}$ for —S=O absorptions.

The structures of Examples IV and VI are:

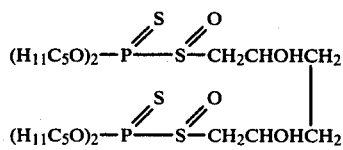

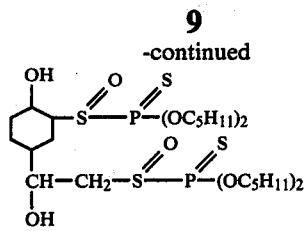

VI

EXAMPLE VII

A mixture of 22.2 g (0.1 mole) of phosphorus pentasulfide and 43.2 ml (0.4 mole) of n-amyl alcohol was stirred at reflux till all of the phosphorus pentasulfide had reacted and dissolved, 2 hours. The hot mixture was blown with $N_2$ to remove the hydrogen sulfide, cooled to 25° C., filtered, and diluted with n-heptane to 200 ml (1 M) in a volumetric flask. A mixture of 100 ml (0.1 mole) of 1 M O,O-diamyl phosphorus dithioic acid, 11 ml (0.1 mole) of 1-pentene, and 10 ml 1% methylene blue in acetone was shaken under 24 psig $O_2$ and light from a 275 watt sunlamp in a reflector for 72 hours, absorbing 6 lbs. $O_2$. It was evaporated at 40° C. and 0.4 Torr. to give 28.3 g of light-yellow viscous oil, 1-(0,0-diamyl dithiophosphoryl sulfoxy)-2-pentanol.

Calcd. for $C_{15}H_{33}PO_4S_2$: C, 50.6; H, 9.3; S, 18.0; P, 8.7

Found: C, 50.3; H, 8.8; S, 18.7; P, 9.4;

The mass spectrum showed a very small peak at the parent (P) mass 327, and much larger peaks at P $-H_2O$, mass 354 and protonated P $-H_2O$, mass 355.

EXAMPLE VIII

A mixture of 11.1 g (0.05 mole) of phosphorus pentasulfide, 37.26 g (0.20 mole) of n-dodecyl alcohol, and 200 ml of n-hexane was stirred and refluxed until all the phosphorus pentasulfide had reacted and dissolved (24 hours). The hot solution was blown with $N_2$ to remove hydrogen sulfide, then cooled. The acid was 0,0-didodecyl phosphorus dithioic acid. It was added to 22.1 ml (0.1 mole) of 1-dodecene and 10 ml of 1% methylene blue in acetone. The mixture was shaken under 24 psig $O_2$ and illumination by a 275 watt sunlamp in a reflector until 7 lbs. $O_2$ absorbed in 72 hours. Evaporation in a Rinco evaporator at 40° C. and 0.2 Torr. yielded 65.6 g of light-yellow viscous oil, 1-(0,0-didodecyl thiophosphoryl sulfoxy)-2-dodecanol.

Calculated for $C_{36}H_{76}S_2PO_4$: C, 64.4; H, 11.3; S, 9.5; P, 4.6;

Found: C, 64.7; H, 11.5; S, 9.4; P, 4.4.

EXAMPLE IX

A mixture of 22.2 g (0.1 mole) of phosphorus pentasulfide, 100 ml of benzene, and 80.8 g (0.4 mole) of n-dodecanethiol was stirred and refluxed 4 hours at which time all the phosphorus pentasulfide had reacted and dissolved. The mixture was cooled. The acid was S,S-n-dodecane phosphorus tetrathioic acid. 23 ml (0.2 mole) of freshly-distilled styrene were added to the acid together with 10 ml of 0.5% methylene blue in acetone. The mixture was shaken under 25 psig $O_2$ and irradiation of a 275 watt sunlamp. After 17 hours, 5 lb. $O_2$ was absorbed. The solution was decanted from 9.2 g of black tarry material and evaporated in a Rinco evaporator at 45° C. and 0.2 Torr. to give 111 g clear, brown, viscous oil with no odor, 1-(S,S-didodecanethiothiophosphoryl sulfoxy)-2-phenyl-2-ethanol.

Calculated for $C_{32}H_{59}S_4PO_2$: C, 60.5; H, 9.7; P, 4.9; S, 20.2

Found: C, 61.3: H, 10.2: P, 4.0; S, 19.4;

EXAMPLE X

S,S-Di-n-dodecyl tetrathiophosphoric acid from 22.2 g of phosphorus pentasulfide and 80.8 g n-dodecanethiol, prepared as in Example IX, was mixed with 21.9 ml (0.2 mole) of 1-pentene and 10 ml of 0.5% methylene blue in acetone. The mixture was shaken under 25 psig $O_2$ and irradiation with a 275 watt sunlamp for 48 hours, absorbing 5 lbs. $O_2$. The solution was decanted from 11.6 g black, tarry material and evaporated in a Rinco evaporator at 45° C. and 0.2 Torr. to give 104.9 g. clear, brown, viscous product, 1-(S,S-di-dodecyl thiothiophosphoryl sulfoxy)-2-pentanol.

Calculated for $C_{29}H_{61}S_4PO_2$: C, 58.0; H, 10.2; P, 5.2; S, 21.3

Found: C, 60.5%; H, 10.0%; P, 4.0%; S, 20.9%

The effectiveness of the novel compounds of my invention as surfactants in lowering interfacial tension between solvent-extracted 5W oil and water was measured, using a Cenco-Du Nouy Interfacial Tensiometer #70545 with a 6 cm platinum-iridium ring at 25° C., with double-distilled water, with these results; all at 1% concentration in 5W oil:

| Product of Example # | Dynes/cm |
|---|---|
| Control | 34.03 |
| I | 10.60 |
| II | 14.03 |
| III | 14.93 |
| IV | 13.73 |
| V | 14.83 |
| VI | 12.74 |
| VII | 9.45 |
| VIII | 1.24 |
| IX | 12.97 |
| X | 5.86 |

The compounds of Example I through X were tested as biocides and inhibitors for the growth of microorganisms by the test: 25 g of agar preparation were placed in standard Petri dishes. The Agar preparation consisted of 23.5 g of Bacto Plate Count Agar, Difco Laboratories, Detroit, Michigan, dissolved in 1 liter of water. Plate Count Agar contains a standard USP formula for nutrient agar, consisting of 5 g Pancreatic digest of casein
2.5 g Yeast extract
1 g Glucose
15 g Agar Four Petri dishes were untreated and used as blanks. To the others, in duplicate, were added 2.5 ml of 1% acetone solutions of the products of Examples I-X. All plates were uncovered for 4 hours to expose them to the spores of adventitious fungi and bacteria, then covered and stored at 30° C. for 6 days. Ratings were given at this point; 0 represents no growth, 5 shows luxuriant colonies of fungi and bacteria. Results are shown in the table.

| Product Example # | Rating |
|---|---|
| I | 0,0 |
| II | 0,0 |
| III | 0,0 |
| IV | 0,0 |
| V | 3,4 |
| VI | 0,0 |

| Product Example # | Rating |
|---|---|
| VII | 0,1 |
| VIII | 0,0 |
| IX | 0,0 |
| X | 0,0 |
| Control | 5,5,5,5 |

The product of Example VIII was tested as an antiwear additive at 1% in SX 5W oil on the 4-ball wear test machine, ASTMD-2266, modified to run at 600 rpm, 200° F., 2 hours with a 40 kg load. Under these conditions SX-5 base oil gives a wear scar af about 0.7 mm. A good zinc dithiophosphate at 1% concentration gives a wear scar of 0.45 mm or less. The product of Example VIII gave a wear scar of 0.52 mm, quite good for a compound containing no metal.

The products from poly-thiophosphoric acid compounds, olefinically unsaturated compounds and oxygen of this invention may be used in solutions and formulations at 0.001% to 10% by weight.

EXAMPLE XI

A mixture of 11.1 g (0.05 mole) of phosphorus pentasulfide, 8.8 ml (0.22 mole) of methanol, and 200 ml of dry benzene was stirred and refluxed until all the phosphorus pentasulfide had reacted and gone into solution (40 hours). The mixture was blown with $N_2$ until the odor of hydrogen sulfide disappeared, then cooled. The acid was 0,0-dimethyl phosphorus dithioic acid. It was stirred with 10 ml of 1% methylene blue in acetone and irradiated with a 275 watt sunlamp in a reflector. Ethylene and oxygen, each at 50 cc/minute, were passed through the benzene solution for three hours. The mixture was evaporated in a Rinco rotary evaporator, giving 19.84 g of viscous, yellow-brown oil (91 mole % yield) of 1-(0,0-dimethyl thiophosphoryl sulfoxy)-2-ethanol.

Analysis: Calculated for $C_4H_{11}PS_2O_4$,

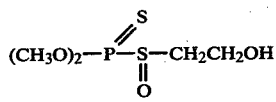

C, 22.0%; H, 5.0%; P, 14.2%; S, 29.4%
Found: C, 21.5%; H, 4.6%; P, 14.5%; S, 29.8%

EXAMPLE XII

The identical procedure and reagents were used as in Example I except that the reaction mixture was not illuminated with a sunlamp bulb in a reflector. This dark reaction absorbed only 2 lb. $O_2$ after 24 hours. It was discarded.

I claim:
1. A beta phosphosulfoxy alcohol compound of the general formula

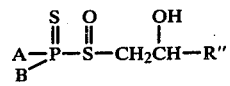

wherein A is selected from the group consisting of RO— and RS—, and B is selected from the group consisting of R'O— and R'S— and wherein R and R' are individually selected from the group consisting of hydrogen and alkyl groups of 1 to 24 carbon atoms, and wherein R" is selected from the group consisting of hydrogen, an alkyl group of 1 to 22 carbon atoms, phenyl, naphthyl, anthranyl, phenanthryl and cyclohexyl moieties, said R and R' being optionally substituted, said substitutions being selected from the group consisting of halogens and nitro moieties, and said R" being optionally substituted, said substitutions being selected from the group consisting of halogen, nitro, methoxy, ethoxy, propoxy, butoxy, dialkylamino, hydrogen, methyl, ethyl and

wherein A and B are defined as herein.
2. The compound of claim 1 which comprises 1-(0,0-diamyl thiophosphoryl sulfoxy)-2-phenyl-2-ethanol.
3. The compound of claim 1 which comprises 1-(0,0-diisoamyl thiophosphoryl sulfoxy)-2-phenyl-2-ethanol.
4. The compound of claim 1 which comprises 1-(0,0-diisoamyl thiophosphoryl sulfoxy)-2-octanol.
5. The compound of claim 1 which comprises 1,6-bis(0,0-diisoamyl thiophosphoryl sulfoxy)-hexane-2,5-diol.
6. The compound of claim 1 which comprises 1-(0,0-diisoamyl thiophosphoryl sulfoxy)-2-(3-cyclohexenyl-1)-2-ethanol.
7. The compound of claim 1 which comprises 1-(0,0-diisoamyl thiophosphoryl sulfoxy)-2-[4-hydroxy-3-(0,0-diisoamyl thiophosphoryl sulfoxy)-cyclohexyl]-2-ethanol.
8. The compound of claim 1 which comprises 1-(0,0-didodecyl thiophosphoryl sulfoxy)-2-dodecanol.
9. The compound of claim 1 which comprises 1-(S,S-didodecanethiothiophosphoryl sulfoxy)-2-phenyl-2-ethanol.
10. The compound of claim 1 which comprises 1-(S,S-didodecanethiothiophosphoryl sulfoxy)-2-pentanol.
11. The compound of claim 1 which comprises 1-(0,0-dimethyl thiophosphoryl sulfoxy)-2-ethanol.

* * * * *